United States Patent [19]

Charlton et al.

[11] Patent Number: 5,520,883
[45] Date of Patent: * May 28, 1996

[54] TEST DEVICES FOR DETERMINATION OF GLUCOSE

[75] Inventors: Steven C. Charlton; Robert P. Hatch; Paul R. Hemmes, all of Elkhart, Ind.

[73] Assignee: Miles Inc., Elkhart, Ind.

[*] Notice: The portion of the term of this patent subsequent to Mar. 10, 2004, has been disclaimed.

[21] Appl. No.: 402,689

[22] Filed: Sep. 5, 1989

Related U.S. Application Data

[62] Division of Ser. No. 119,977, Nov. 13, 1987, Pat. No. 4,895,798.

[51] Int. Cl.$^6$ ..................................................... G01N 33/50
[52] U.S. Cl. ................. 422/56; 422/61; 435/14; 436/14; 436/95; 436/169
[58] Field of Search ............ 435/14, 28; 422/55–58, 422/61; 436/14, 95, 164, 169, 904

[56] References Cited

U.S. PATENT DOCUMENTS

| | | | |
|---|---|---|---|
| 3,252,762 | 5/1966 | Adams et al. | 436/66 X |
| 3,668,076 | 6/1972 | Rey et al. | 422/56 X |
| 3,920,580 | 11/1975 | Mast | 436/14 |
| 3,964,871 | 6/1976 | Hochstrasser | 435/14 X |
| 4,017,261 | 4/1977 | Svoboda et al. | 436/66 X |
| 4,046,514 | 9/1977 | Johnston et al. | 436/95 X |
| 4,220,713 | 9/1980 | Rittersdorf et al. | 435/14 |
| 4,234,316 | 11/1980 | Hevey | 436/95 X |
| 4,385,114 | 5/1983 | Guthlein et al. | 435/28 |
| 4,541,987 | 9/1985 | Guaclagno | 422/61 |
| 4,649,121 | 3/1987 | Ismail et al. | 435/14 |
| 4,654,310 | 3/1987 | Ly | 436/164 |

FOREIGN PATENT DOCUMENTS 3541979  6/1987  Germany.

OTHER PUBLICATIONS

Research Disclosure, Jun. 1978, pp. 25–27, disclosure No. 17031.

*Primary Examiner*—Lyle A. Alexander
*Attorney, Agent, or Firm*—Roger N. Coe

[57] ABSTRACT

Test devices are disclosed which are useful for determining glucose or occult blood comprising a carrier matrix, glucose oxidase, an indicator system and a glucose derivative that upon addition of water hydrolizes to produce glucose.

4 Claims, No Drawings

TEST DEVICES FOR DETERMINATION OF GLUCOSE

This is a division of application Ser. No. 119,977, filed on 13 Nov. 1987, now U.S. Pat. No. 4,895,798.

FIELD OF THE INVENTION

The invention relates to unitary, solid state test devices for the determination of occult blood and glucose. More particularly, the invention relates to test devices incorporating, as a component of the system, a glucose derivative that upon contact with water hydrolizes to produce glucose.

BACKGROUND OF THE INVENTION

Solid state test devices useful for the determination of glucose are widely used in hospitals, clinical laboratories, physician's offices and in the homes of patients. After manufacture, such test devices are packaged and shipped from the manufacturer's controlled storage facilities. Each package can then be subjected to different stress conditions, such as heat, humidity, and light, which adversely affect the viability of the test composition. A test device that can be conveniently tested by the user to determine the validity of the test results is therefore desirable. As glucose testing is often done by relatively untrained persons, a glucose test device which provides the user with a test for the viability of the test composition is particularly useful.

A need also exists for a simple, quick test for the detection of microscopic amounts of blood (occult blood) in feces and urine.

Glucose Determination

Solid state test devices for the determination of glucose are known. Such test devices take the form of a test composition comprising glucose oxidase and an indicator system incorporated within a carrier matrix. Control and viability tests for such test systems are also known. U.S. Pat. No. 3,920,580 is exemplary of control systems wherein the test system is checked with a separately provided control composition. The control composition contains analyte which is reactive with the test system or an analyte analog which reacts readily with water to produce the analyte (e.g., easily hydrolized esters of the reactive analyte or its analog). The control composition can be available in liquid form, ready for use, or in a powder form which, when dissolved in a predetermined quantity of water, forms a control solution of known concentration.

Also available are control test devices wherein a carrier matrix is incorporated with the control composition. The control device delivers a known quantity of analyte or analog thereof into a predetermined quantity of water, or appropriate solvent, to form a control solution of known concentration. An example of such a control test device is illustrated in U.S. Pat. No. 4,234,316.

Occult Blood Tests

A number of test systems for the determination of occult blood are known. These test systems rely on the detection of the peroxidase activity of hemoglobin. Such test systems are known in the form of test strips. Such strips typically include an indicator or chromogen and a hydroperoxide compound in addition to various buffers and stabilizers.

One problem in such systems is the prevention of premature oxidation of the chromogen by the hydroperoxide compound. The prior art has suggested several methods of preventing such a premature reaction. For example U.S. Pat. No. 3,252,762 describes utilizing an encapsulated organic hydroperoxide.

U.S. Pat. No. 4,017,261 discloses the use of amine salts of organic hydroperoxides in test strips. A carrier, such as filter paper, is first impregnated with an aqueous solution of buffer and chromogen and then thoroughly dried. The carrier is then impregnated with a non-aqueous solution of an amine salt of organic hydroperoxide compound and again dried. When the strip is placed in an aqueous solution the components come in to contact with one another and the hydroperoxide is freed from its salt by the action of the buffer.

Glucose Boronates and Borinates

Boronate and borinate derivatives of sugars are documented in the chemical literature. See, e.g., R. J. Ferrier, *Advanced Carbohydrate Chemistry and Biochemistry*, 35, 31 (1978). Boronate derivatives are known to be nonpolar and to hydrolize rapidly with water. See, J. M. J. Frechet, L. J. Nuyens and E. Seymour, *Journal of American Chemistry Society*, 101, 432 (1979).

SUMMARY OF THE INVENTION

The invention provides a solid state unitary device useful for determining glucose comprising:

(a) a carrier matrix;

(b) a test composition for the determination of glucose incorporated substantially uniformly within the carrier matrix, said test composition being capable of providing a detectable optical response upon wetting of the carrier matrix with an aqueous glucose solution; and (c) a glucose derivative incorporated in at least a portion of the test composition incorporated carrier matrix, at a concentration sufficient to provide a detectable optical response in the doubly incorporated carrier matrix upon wetting of the matrix with water.

The glucose test device can be provided as a control device when the glucose derivative is incorporated substantially uniformly with the entire test composition within a carrier matrix. When the glucose derivative is incorporated with a limited defined portion of the test composition within a carrier matrix, the viability device becomes an internal control device. The internal control device is capable of providing a detectable optical response when wetted with water thus indicating the viability of the incorporated test composition. The internal control area does not interfere with the use of such a device in the determination of glucose in an aqueous fluid sample. By incorporating the glucose derivative at different concentrations in a plurality of limited defined portions of the test composition incorporated matrix, a self-indicating device can be provided. The incorporated glucose derivative concentrations can be chosen to be clinically significant concentrations of glucose. A self-indicating device can also be provided by attaching a plurality of internal control devices, each incorporated with different glucose derivative concentrations to a support member.

The invention also provides a solid state unitary test device useful for the determination of occult blood. The test device comprises a test composition comprising a glucose derivative that upon addition of water produces glucose, glucose oxidase and an oxidation indicator system.

DETAILED DESCRIPTION

Test Device Components

A. Glucose Derivatives

The two-test devices, occult blood and glucose, described herein, have as a common ingredient a glucose derivative that upon contact with water produces glucose. To have utility in this test device, the glucose derivative must be soluble in an organic solvent, be nonreactive with other strip reagents and hydrolize rapidly with water to produce glucose.

One such class of glucose derivatives are the glucose boronates. Glucose boronates can be represented by the following generalized formula:

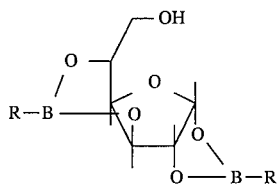

wherein R is alkyl, aryl or alkylaryl. The hydrocarbon groups can be substituted so long as the substituents do not detract from the necessary qualities stated above and do not in some manner interfere with the detection mechanism of the test device. Preferably R is selected from the group consisting of alkyl hydrocarbons of 1 to 8 carbon atoms, phenyl groups and substituted phenyl groups wherein the substituent is an alkyl group of 1 to 4 carbon atoms.

Glucose boronates can be prepared by the reaction of glucose with either an acid or anhydride. The reaction can be represented as below:

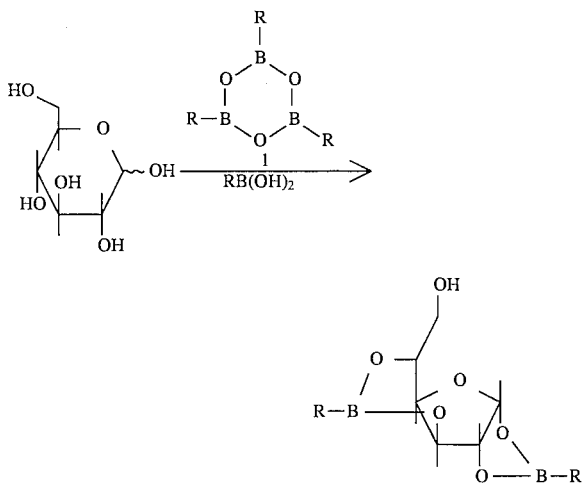

wherein R is defined as above.

EXAMPLE I 1,2:3,5-bis(phenylboronate)-2-D-glucofuranose

Phenylboronic anhydride was first prepared by refluxing a solution of the acid (1.35 gm, 11.1 mmol) and 40 milliliters (ml) of $CCl_4$ and then removing the water layer. The solvent was evaporated and the residue dissolved in 5 mls of methanol. The mixture was added drop-wise to a solution of glucose (1.0 gm, 5.6 mmol) in 10 ml of methanol. The reaction was allowed to stir overnight under argon and the solvent removed to yield 2.1 grams (gms) of a white solid.

EXAMPLE II 1,2:3,5-bis(butylboronate)-2-D-glucofuranose

A mixture of glucose (0.5 gms, 2.8 mmol) and butaneboronic acid (0.86 gms, 8.4 mmol) and 10 ml of pyridine was refluxed for 15 minutes. The solvent was removed in vacuo. The residue was dissolved in 50 ml of toluene and then the solvent evaporated to yield 0.68 gms of a pale yellow oil.

Both the phenyl and butyl compounds meet the previously set forth criteria. They are soluble in organic solvents, hydrolize easily to produce glucose and do not react with other reagents in the occult blood test device or the glucose test device.

Another class of glucose derivatives suitable for use in the test devices of this invention are the alkyl and aryl borinates. These compounds can be represented by the formula:

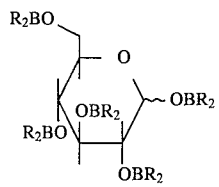

wherein R is as described above. Glucose borinates are prepared from the reaction of glucose and trialkyl and triaryl boranes.

B. Glucose Oxidase

Both test devices utilize the enzyme glucose oxidase. Glucose oxidase oxidizes glucose to gluconolactone in the presence of molecular oxygen.

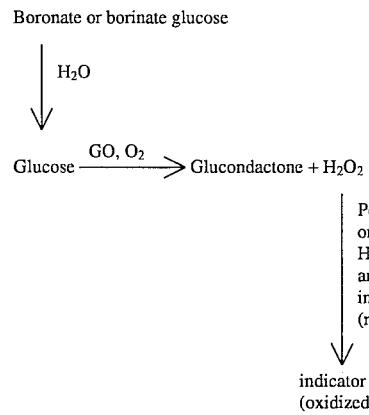

C. Carrier Matrix

The carrier matrix can be any substance capable of being incorporated with the components of the test composition, as long as it is substantially inert with respect to the test composition, porous and/or absorbent relative to the aqueous sample to be tested. The expression "carrier matrix" refers to either bibulous or nonbibulous matrices which are insoluble in and maintain their structural integrity when exposed to water or other physiological fluids. Suitable bibulous matrices which can be used include paper, cellulose, wood, synthetic resin fleeces, woven and nonwoven fabrics and the like. Nonbibulous matrices include glass fibers, polymer films, preformed or microporous membranes, organic plastic materials such as polypropylene and the like.

In producing a test device of the invention, all such carrier matrix concepts can be employed as can others. The matrix can include a system which physically entraps any or all of these ingredients, such as polymeric microcapsules which rupture upon contact with an aqueous solution. The matrix can also comprise a layered system wherein each composition component is homogeneously combined in a fluid or a semifluid state, which later hardens or sets, thereby entrapping the ingredients until wetted by the aqueous sample. Other matrix formats are contemplated, including the use of commercially available preformed porous membranes or microporous membranes formed by techniques such as phase inversion. Polymer film matrices such as films produced by latex formulations based on a latex polymer suspensions, for example the 60:40 copolymer of styrene and butadiene, or other natural or synthetic polymers or mixtures thereof can be used. Examples of such film formulations can be found in U.S. Pat. Nos. 3,630,957 and 4,312,834, both of which are incorporated herein by reference.

A unitary solid state test device can be prepared by incorporation of a test composition within a carrier matrix, with drying between successive incorporation steps. Incorporation of the test composition can be accomplished by any method such as spreading, spraying, or dipping, a process often called impregnation, which allows the carrier matrix to be incorporated with a viable test composition reactive with the analyte of interest.

D. Indicator System

Both test devices rely on indicators or indicator systems to provide a detectable response. To be useful, the indicator system should oxidize under normal test conditions, and typically should absorb light, when oxidized, at a wavelength greater than 580 nanometers (nm). The indicator system can be a single compound or have multiple components. Suitable indicators include compounds that when oxidized can couple with itself or with its reduced form to produce a dye. Such auto coupling compounds include o-aminophenols, 4-alkoxynaphthols, 4-amino-5-pyrazolones, cresols, pyrogallol, guaiacol, orcinol, catechol, chloroglucinol, p-dihydroxydiphenylgallic acid, pyrocatechoic and salicylic acid. Compounds of this type are well known. See, e.g., *The Theory of the Photographic Process*, Mees and James, 3rd Ed. (1966), Ch. 17.

Other indicators include leuco dye compounds. Representative leuco dyes include triarylimidazole dyes (see, e.g., U.S. Pat. No. 4,089,747) and triarylmethaneleuco dyes.

Still another group of indicator systems are based on the color forming reaction between an oxidizable compound and a coupler. Representative oxidizable compounds include benzidine and its homologues, p-phenyldiamines, p-aminophenols, aminoantipyrines and the like. A number of couplers can be used with such compounds so long as they, in connection with the oxidizable compound, produce a compound that absorbs light at greater than 580 nm.

In the case of the glucose test device, the indicator system includes a peroxidative (e.g., peroxidase), an aminoantipyrine oxidizable compound (e.g., 4-aminoantipyrine) and a coupler which will react with the aminoantipyrine in its oxidized state.

In addition to the compounds previously mentioned, other suitable couplers include toluidines, such as n-ethyl-n-2-sulfoethyl-m-toluidine, n-ethyl-n-2-carboxyethyl-m-toluidine, n-2-carboxyethyl-m-toluidine, n-sulfoethyl-p-toluidine, n-methyl-n-(2,3-dihydroxypropyl)-m-toluidine. Other useful couplers include dihydroindoles, tetrahydraondoles, tetrahydroquinolines and substituted aniline compounds such as 8-anilino-1-naphthalenesulfonic acid and n-methyl-n-sulfopropylaniline.

SELF INDICATING-GLUCOSE TEST DEVICE

Commercially available glucose test devices are intended as single use, throw-away devices. Testing of a single viability test device by wetting with water indicates the viability of the glucose test composition incorporated therein and is expected to provide an indication of other test devices in the consumer's hands which have been stored under the same or similar conditions. For example, testing of a viability test device taken from a bottle of similar devices stored in a bathroom medicine cabinet, if positive, would indicate the viability of the other test devices in the bottle. Those other devices, if of the internal control or self-indicating type, can be used to determine the concentration of glucose in an aqueous solution.

According to the present invention, a viability test device can be prepared by incorporating a glucose derivative that hydrolizes to form glucose within a carrier matrix which has been incorporated with a test composition reactive with glucose. The viability test device can be prepared in three formats depending on the area incorporated with glucose derivative, the concentration of glucose derivative and the configuration or number of glucose derivative incorporated matrices used for a single device. The viability test device indicates the viability of the test composition by the detectable response produced when the device is wetted by ordinary water or any aqueous fluid devoid of glucose. If the test composition has deteriorated so that it is unable to produce a response to the glucose produced by the hydrolysis of the glucose derivative, there will be no detectable response when the device is wetted with water. The presence of this detectable response is a positive indication that the test device and indeed any test device stored with it, can provide a viable test for glucose. When a home user contacts a sample with a diagnostic test device, the preferred (normal) response is often a negative (i.e., devoid of glucose) response. This is particularly true with diabetics where normal glucose concentrations should be very low. At present, the home user is left to wonder if the sample was truly negative, as desired, or if the diagnostic test device had deteriorated due to storage conditions and no longer provides a detectable response.

A. Formats (1) Control Device

The viability test device can be prepared as a control device by incorporating substantially the entire test composition incorporated carrier with the glucose derivative. Such a test device can be included in a bottle or vial of purchased ordinary diagnostic glucose test devices containing only the glucose test composition, which will be stored under similar conditions by the ultimate consumer. Testing of that control device by contacting it with water and observing the detectable response visually or instrumentally assures the user that other strips, purchased at the same time and stored under similar conditions, will provide a viable test for glucose.

(2) Internal Control Device

A particularly convenient format for the viability test device is that of an internal control device wherein the glucose derivative is incorporated within a limited defined portion of the test composition incorporated carrier. The user can be assured that the strip provides a viable test for glucose since a detectable response is produced in a defined limited portion of the device even when wetted by a negative sample if the test composition is viable. An internal control test device can be used as a diagnostic test device since the incorporated glucose derivative does not interfere with the ability of the device to assay an aqueous test sample.

(3) Self-Indicating Device

A self-indicating test device can also be prepared according to the present invention. A test composition incorporated carrier can be incorporated with the glucose derivative at one or more concentrations in separated defined portions of the carrier. Although the self-indicating glucose test device can act as a viability test device, it also provides a great deal more information. When contacted by a test sample containing glucose, the concentration range of the glucose can be determined by comparing the detectable response produced in substantially the entire device with the response in the areas incorporated with the glucose derivative. The self-indicating device is particularly useful when the detectable optical response is color so that the responses can be determined visually. Such a device can be advantageously used to allow immediate recognition of the normal clinical range of glucose.

A self-indicating device can also be prepared by utilizing multiple internal control matrices affixed to a single support member. Such a support member can be made of a variety of polymeric materials as is well known in the art. The glucose derivative can be incorporated within a limited defined area of each matrix at a different concentration level. When the device is contacted with a test sample, the concentration level of the sample can be estimated to be between the highest glucose derivative concentration in which detectable response in the control area is substantially indistinguishable from the rest of the reactive matrix and the incorporated glucose derivative concentration of the matrix in which the control area detectable response is distinguishable from the background detectable response.

B. Optical Response

The glucose derivative must be incorporated within the carrier matrix at a concentration sufficient to provide a detectable optical response when the device is wetted with tap water or distilled water devoid of glucose.

The detectable response can be fluorescent or color. In a preferred embodiment, the optical response is color which can be detected and the device visually or by reflectance reading with a spectrophotometer such as a reflectance photometer available from Miles Laboratory, Inc., Elkhart, Ind.

Test devices designed to determine glucose are based on kinetic reactions where a colorometric end point is determined a specified time after contact with the sample. That time, called the normal read time for the test device, is usually chosen at a time point which provides the greatest color differentiation between concentration levels of sample glucose which the device is designed to determine. The incorporated glucose derivative in this invention should provide a detectable optical response within the normal read time for the test composition incorporated carrier. Usually, glucose test devices presently available have a normal read time of less than about two minutes, and preferably one minute or less.

C. Incorporation of the Glucose Derivative

The glucose derivative can be incorporated within the test composition incorporated carrier matrix in any manner which will be prevent premature interaction with the test composition, but allow substantially immediate interaction of the glucose produced by the hydrolysis of the glucose derivative and test composition once the carrier is wetted with water. This can be done in a number of ways, including microencapsulation of the glucose derivative and deposition onto the dried carrier previously incorporated with the test composition; commonly employed printing techniques such as jet printing; or by the controlled deposition of a solution or suspension of the glucose derivative in a dried nonaqueous organic solvent. If the solution or suspension is incorporated substantially uniformly with the entire dried test composition incorporated carrier, a viability test device useful as a control or calibrator device is formed.

A viability test device useful as an internal control device can be formed by incorporating the glucose derivative within a limited defined portion of the dried test composition incorporated carrier. Incorporation can be accomplished by any of the methods mentioned above. Although it was originally believed that the capillary action of a carrier, particularly a paper carrier, would spread the glucose derivative over the whole matrix, it has been found that a solution or suspension can be controlled to allow incorporation with a limited defined area as desired. The solution or suspension can be placed onto the dried carrier with a syringe, pipette or similar device capable of delivering controlled quantities of solutions or suspensions.

It is particularly preferred to incorporate the glucose derivative in a solution, since the concentration of the glucose derivative incorporated can be controlled more easily when a true solution is used. In either case, whether a solution or suspension is used, care must be taken to use nonaqueous organic solvents which are dried (i.e., free from any water). If water remains in the solvent, the glucose derivative could hydrolyze, prematurely producing glucose and also causing premature interaction between the test composition and the glucose. The solvent can be dried by any of the methods well known to organic chemists.

The area of incorporation of the unreacted analyte can be any convenient geometric shape, for example, half the matrix, a letter, or number or a dot. It is preferred that the internal control portion be a fine, offset line or a small dot on the matrix in order that the optical response of the internal control not interfere with the optical response in the remainder of the device when the device is used with an aqueous fluid sample as a test solution for the determination of glucose.

The concentration of incorporated glucose derivative can be chosen as desired. It is preferred to choose a low concentration of glucose derivative which will provide a detectable optical response when wetted with water, which response becomes virtually indistinguishable from the test composition response upon contact with a sample containing glucose concentration approximately the same or higher than the incorporated glucose concentration.

A self-indicating device can be formed by incorporating two or more limited defined portions of a test composition incorporated carrier with different glucose derivative concentrations. Practically, due to the size of the test devices normally employed, a single carrer matrix can preferably be incorporated with two different concentrations of glucose derivative at different defined areas of the dried carrier. If more concentration markers are desired, a larger carrier can be used or multiple carriers, each incorporated with a different concentration of glucose derivative, can be fixed to a support member to provide a unitary test device.

With glucose, it is particularly preferred that the optical response provided by the concentrations used correspond to the optical response of clinically significant concentrations such as the high and low end of the so-called normal clinical range of glucose; thus giving the user a fast, convenient indication that additional testing may be required. The concentration of glucose must be carefully chosen to provide a detectable optical response equivalent to that seen in a clinical sample. This concentration can be determined experimentally and is usually very close to, but slightly less than, the sample glucose concentration desired.

For example, it can be desirable to have a self-indicating test device for urinary glucose prepared so that the user will know if the sample values obtained are within a specific range, for example 30 to 100 milligrams/deciliter (mg/dL). Commonly available glucose test devices are generally composed of a carrier matrix incorporated with glucose oxidase and an indicator system such as peroxidase and 3,3',5,540 -tetramethylbenzidine. The self-indicating test device can be prepared by incorporating such a glucose test device with a low concentration of glucose derivative which provides a detectable optical response when wetted with water. When a second device so constructed is contacted with a urine sample containing 30 mg/dL glucose, the optical response is indistinguishable from the response in the entire device, within the normal read time for the test composition incorporated matrix. A second incorporated glucose derivative concentration would provide a response which is detectable when wetted with water but which is indistinguishable from the response in the entire device in the normal read time, when a second device so constructed is contacted with sample which contains more than 100 mg/dL glucose. Therefore, if both control areas are visible, the sample contains less than 30 mg/dL glucose; if one control area is visible, the sample contains a glucose concentration within the specified range; and if neither control area is visible, the sample contains a concentration of glucose above the specified range. In the latter case, treatment and/or additional testing may be indicated.

Drying of the matrix after the incorporation of the glucose derivative can be accomplished by any means which will not adversely affect the incorporated glucose derivative or test composition. Usually the drying is carried out by means of an air oven. The dried paper can thereafter be cut and mounted on one end of a support member, for example, a rigid or semi-rigid polystyrene film strip. Mounting of the paper on the strip can be accomplished by use of a double faced adhesive tape, such as that commercially available from the 3M Company, St. Paul, Minn. as DOUBLE STIK®. The support member provides a convenient handle which facilitates use of the test.

EXAMPLE III

Glucose Control Strips

A solution of 100 mg/dL of glucose his phenylboronate and dry methylene chloride was prepared and applied to CLINISTIX® glucose test strip pad. No color development was observed. The pads were then wetted with water and in 2 or 3 minutes color development was observed. Glucose his butylboronate was similarly applied to CLINISTIX® strips. Again no color was observed upon application. After wetting with water strong color development was observed in 10 to 15 seconds.

OCCULT BLOOD TEST DEVICE

The occult blood test device comprises a test composition incorporated into a carrier matrix. The carrier matrix has previously been described. The test composition comprises a glucose derivative that upon addition of water produces glucose, glucose oxidase and an oxidation indicator system.

When the test device is treated with an aqueous solution of hemoglobin, the glucose derivative is hydrolyzed to form glucose. The glucose then reacts with the glucose oxidase to form gluconolacotone and hydrogen peroxide. Any hemoglobin present reacts with the hydrogen peroxide to form an oxidizing species which oxidizes the indicator to produce an optically detectable response. The optical response is proportiaonal to the amount of hemoglobin in the sample.

The process can be represented by the following scheme wherein GB is a glucose boronate, GLU is glucose, GO is glucose oxidase, IND is an indicator and (ox) represents an oxidized state of the indicator:

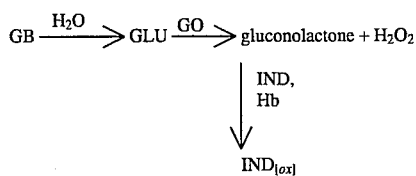

Preferably the occult blood strips are formulated by using two dips to apply the components of the test system. After each dip the strips are dried at 60° C. in an oven. The first dip is an aqueous solution of glucose oxidase. The solution may contain other ingredients such as color stabilizers, emulsifiers, and components of the indicator system. Following impregnation with the first dip the strip is dried and then dipped in a second solution. The second solution is a solution of the glucose derivative in a dried organic solvent. The solvent must be free of water to prevent premature hydrolysis of the glucose derivative. This solution may also contain additional components such as elements of the indicator system.

The operation of the occult blood test is optimal in a pH range between 5.3 and 6.8. Thus it is critical that solutions being tested be treated with a buffer to maintain their pH in this range. The preferred buffers are 2,2-bis(hydroxymethyl)-2-2'-2"-nitrilotri-ethanol (BIS-TRIS), citrate and morpholineethane sulfonic acid, all with their pH's adjusted between 5.3 and 6.8.

In the following examples, strips were prepared with two dips of the composition shown below. These strips were then treated with buffered solutions of hemoglobin (Hb) of known concentrations. The identity of the buffer in each case is also identified below. The optical signal was detected by reflectance at 640 nm and the data recorded in K/S. This is the product of the following mathematical equation:

$$K/S = \frac{(1-R)^2}{2R},$$

where R equals reflectance.
Three values of K/S are listed for each concentration. These values are from different strips formulated in an identical manner.

EXAMPLE 4

| Dip 1 | Dip 2 |
| --- | --- |
| 10 mL H$_2$O<br>0.5 g (245 U/mg)<br>glucose oxidase | 10 mL acetone<br>.06 g tetramethylbenzidine<br><br>100 mg glucose bis<br>butylboronate |

Buffer: 200 mM Bis-Tris, 100 mg/dL albumin, pH 6.3

| K/S | Concentration Hb |
|---|---|
| .093677 | 5 mg/dL |
| .093212 | |
| .085831 | |
| .1749 | 10 mg/dL |
| .15704 | |
| .15121 | |
| .51351 | 25 mg/dL |
| .46154 | |
| .45493 | |
| 1.1987 | 50 mg/dL |
| 1.0212 | |
| .82646 | |
| 1.8914 | 100 mg/dL |
| 1.7429 | |
| 1.7336 | |

EXAMPLE 5

| Dip 1 | Dip 2 |
|---|---|
| 20 mL H$_2$O | 20 mL acetone |
| 0.5 g (245 U/mg) glucose oxidase | 0.12 g tetramethylbenzidine |
| .02 g 2-sulfosuccinic acid (a color stabilizer) | 200 mg glucose bis butylboronate |

Buffer: 200 mM Bis-Tris, 100 mg/dL albumin, pH 6.3

| K/S | Concentration Hb |
|---|---|
| .079421 | 5 mg/dL |
| .072548 | |
| .07238 | |
| .22419 | 10 mg/dL |
| .18515 | |
| .14008 | |
| .94881 | 25 mg/dL |
| .946 | |
| .82853 | |
| 2.176 | 50 mg/dL |
| 2.0266 | |
| 1.7724 | |
| 4.1656 | 100 mg/dL |
| 4.124 | |
| 3.8858 | |

EXAMPLE 6

| Dip 1 | Dip 2 |
|---|---|
| 25 mL H$_2$O | 20 mL acetone |
| 0.162 g (245 U/mg) glucose oxidase | .200 g glucose bis butylboronate |
| 0.1 g polyvinyl alcohol (an emulsifer) | |
| 0.135 g 4-aminoantipyrine | |
| .068 g primaquine diphosphate | |

Buffer: 200 mM morpholineethanesulfonate (MES), 100 mg/dL albumin, pH 5.0

| K/S | Concentration Hb |
|---|---|
| .068342 | 0 |
| .068308 | |
| .068115 | |
| .49821 | 5 mg/dL |
| .44865 | |
| .42895 | |
| .79168 | 10 mg/dL |
| .77232 | |
| .75282 | |
| 1.5078 | 25 mg/dL |
| 1.2393 | |
| 1.2001 | |
| 1.6009 | 50 mg/dL |
| 1.3906 | |
| 1.3452 | |
| 1.7174 | 100 mg/dL |
| 1.5474 | |
| 1.2619 | |

The foregoing examples and descriptions are intended to aid the reader in understanding the present invention. While the examples serve to illustrate the invention, they are not to be interpreting as limiting its scope. One skilled in the art will be able to make such variations, substitutions and changes in the composition, ingredients and reaction parameters as desirable.

What is claimed:

1. A test device useful for determining glucose comprising:

a single layer carrier matrix;

a test composition for the determination of glucose incorporated substantially uniformly within the carrier matrix, said composition producing a detectable optical response upon wetting with an aqueous solution of glucose; and a glucose derivative selected from the group consisting of glucose boronates and glucose borinates, which upon contact with water produces glucose, incorporated in a limited, defined portion of said carrier matrix at a concentration sufficient to provide a detectable optical response in said carrier matrix upon the wetting of said matrix with an aqueous solution.

2. The test device of claim 1, wherein each detectable optical response is color.

3. The test device of claim 1, in which the glucose derivative is incorporated within a plurality of limited, defined portions of said carrier matrix, each glucose derivative being incorporated at a different concentration, and each glucose derivative being incorporated at a concentration sufficient to provide a detectable optical response upon the wetting of said matrix with an aqueous solution.

4. The test device of claim 3, in which the plurality of incorporated glucose derivative concentrations provide clinically significant concentrations of glucose when the carrier matrix is wetted with an aqueous solution.

* * * * *